US009517360B2

United States Patent
Ortega et al.

(10) Patent No.: US 9,517,360 B2
(45) Date of Patent: Dec. 13, 2016

(54) NITROCELLULOSE-FREE NAIL POLISH COMPOSITIONS

(75) Inventors: Luis Ortega, Englewood, NJ (US); Hy Si Bui, Piscataway, NJ (US); Ram Hariharan, Springfield, NJ (US); Mohamed Kanji, Edison, NJ (US)

(73) Assignee: L'OREAL, Paris (FR)

( * ) Notice: Subject to any disclaimer, the term of this patent is extended or adjusted under 35 U.S.C. 154(b) by 341 days.

(21) Appl. No.: 12/770,886

(22) Filed: Apr. 30, 2010

(65) Prior Publication Data

US 2010/0278766 A1  Nov. 4, 2010

Related U.S. Application Data

(60) Provisional application No. 61/175,194, filed on May 4, 2009, provisional application No. 61/175,135, filed on May 4, 2009.

(51) Int. Cl.

| | | |
|---|---|---|
| *A61Q 3/02* | (2006.01) | |
| *A61Q 3/00* | (2006.01) | |
| *A61K 8/81* | (2006.01) | |
| *A61K 8/84* | (2006.01) | |
| *A61K 8/85* | (2006.01) | |
| *A61Q 17/00* | (2006.01) | |

(52) U.S. Cl.
CPC ............... *A61Q 3/02* (2013.01); *A61K 8/8164* (2013.01); *A61K 8/84* (2013.01); *A61Q 3/00* (2013.01); *A61K 8/85* (2013.01); *A61Q 17/00* (2013.01)

(58) Field of Classification Search
CPC ............ A61Q 3/02; A61Q 1/02; A61Q 17/00; A61K 8/84; A61K 8/8164; A61K 2800/43; A61K 2800/594; A61K 8/044; A61K 8/90; A61K 2800/95; A61K 8/8147; A61K 8/8158
See application file for complete search history.

(56) References Cited

U.S. PATENT DOCUMENTS

| | | | |
|---|---|---|---|
| 4,293,542 A | | 10/1981 | Lang et al. |
| 4,649,045 A | * | 3/1987 | Gaske et al. .................. 424/61 |
| 6,106,820 A | * | 8/2000 | Morrissey et al. ........ 424/78.18 |
| 2004/0202688 A1 | * | 10/2004 | Mougin et al. ............... 424/401 |
| 2004/0265251 A1 | | 12/2004 | Lee et al. |

FOREIGN PATENT DOCUMENTS

| | | | |
|---|---|---|---|
| DE | 102006062439 A1 | * | 7/2008 |
| EP | 0303803 A2 | | 2/1989 |
| EP | 0346486 A1 | | 12/1989 |
| JP | H09202715 | * | 8/1997 |
| JP | H09202715 A | | 8/1997 |
| WO | 90/12829 A1 | | 11/1990 |

OTHER PUBLICATIONS

Hercules, Scripset® Copolymer Resin, Global Product Offering, www.herc.com/ventures, Sep. 2007.
Sartomer, Technical Data Sheet: SMA® 1000, Styrene Maleic Anhydride Copolymer, Mar. 2008, Sartomer Company, Inc., Oaklands Corporate Center, 502 Thomas Jones Way, Exton, PA, 19341, www. Sartomer.com.
Sartomer, Technical Data Sheet: SMA® 2000, Styrene Maleic Anhydride Copolymer, Mar. 2008, Sartomer Company, Inc., Oaklands Corporate Center, 502 Thomas Jones Way, Exton, PA, 19341, www. Sartomer.com.
Sartomer, Technical Data Sheet: SMA® 2021, Styrene Maleic Anhydride Copolymer, May 2006, Sartomer Company, Inc., Oaklands Corporate Center, 502 Thomas Jones Way, Exton, PA, 19341, www. Sartomer.com.
Rohm and Haas, Industrial Coating, Paraloid™ B-66, Solid Grade Thermoplastic Acrylic Resin, Oct. 1996.
Unitex, Chemical Corporation, Uniplex 670-P, CAS No. 28407-73-0/123-86-4, Issued Feb. 10, 1998, Unitex, Chemical Corporation, P.O. Box 16344, 520 Broome Road, Greensboro, NC 27406.
European Search Report issued on Jun. 12, 2013 in Munich.
Congress Must Expand Protections against Widely Used Harmful Chemicals: Methylene Chloride, Natural Resources Defense Council Jul. 2010, NRDC Facsheet; http://www.nrdc.org/health/files/methyleneChloride.pdf.
European Patent Office, EP Application 10 161 900.5-1458, Communication pursuant to Article 94(3) EPC dated Feb. 11, 2014.

* cited by examiner

*Primary Examiner* — Isis Ghali
(74) *Attorney, Agent, or Firm* — Oblon, McClelland, Maier & Neustadt, L.L.P.

(57) ABSTRACT

The present invention relates to a nail polish composition, comprising at least one high gloss film forming agent chosen from an esterified styrene maleic anhydride copolymer, a non-esterified styrene maleic anhydride copolymer and mixtures thereof, at least one co-film forming agent chosen from an epoxy resin, optionally, at least one plasticizer, at least one solvent, and optionally, at least one colorant, wherein the composition does not require use of nitrocellulose and can be used to makeup or protect nails. Such compositions impart high gloss, good adhesion and long wear properties.

6 Claims, No Drawings

NITROCELLULOSE-FREE NAIL POLISH COMPOSITIONS

CLAIM OF PRIORITY

This application claims the benefit of priority under 35 U.S.C. sctn. 119(e) from U.S. provisional application Ser. No. 61/175,194, filed May 4, 2010 and 61/175,135, filed May 4, 2010, incorporated herein by reference in their entirety.

FIELD OF THE INVENTION

The present invention relates to nail polish compositions for application to nails comprising at least one optionally-esterified styrene maleic anhydride copolymer. Preferably, the compositions are free of, or substantially free of, nitrocellulose. Such nail polish compositions are safer than, and have comparable or better adhesion properties than, traditional nail polish compositions.

DISCUSSION OF THE BACKGROUND

Nail polish compositions traditionally contain a large amount of nitrocellulose, primarily because nitrocellulose provides good adhesion of the compositions to nails upon application. That is, nitrocellulose is the preferred adhesive agent for use in nail polish compositions, and constitutes the "gold standard" of adhesive agents in nail polish compositions. However, nitrocellulose has drawbacks, particularly with respect to consumer safety. Also, nail polish compositions containing nitrocellulose can have poor long wear characteristics. Further, nitrocellulose does not impart high gloss. As a result, alternatives to nitrocellulose-based nail polish compositions have been sought. Unfortunately, to date, such alternatives have been elusive, and commercial nail polish compositions typically contain large amounts of nitrocellulose.

There remains a need for nail polish compositions which are safe, glossy, and adhere well to nails and, ideally, contain minimal amounts of nitrocellulose, if any.

SUMMARY OF THE INVENTION

The present invention relates to a nail polish composition, comprising at least one high gloss film forming agent chosen from an esterified styrene maleic anhydride copolymer, a non-esterified styrene maleic anhydride copolymer and mixtures thereof, at least one co-film forming agent chosen from an epoxy resin, optionally, at least one plasticizer, at least one solvent, and optionally, at least one colorant, wherein the composition does not require use of nitrocellulose.

The present invention further relates to a method of making up or protecting nails comprising applying onto the nails a nail polish composition, comprising at least one high gloss film forming agent chosen from an esterified styrene maleic anhydride copolymer, a non-esterified styrene maleic anhydride copolymer and mixtures thereof, at least one co-film forming agent chosen from an epoxy resin, optionally, at least one plasticizer, at least one solvent, and optionally, at least one colorant, wherein the composition does not require use of nitrocellulose.

It has been surprisingly found by the inventors that the combination of a high gloss film forming agent chosen from an esterified styrene maleic anhydride copolymer, a non-esterified styrene maleic anhydride copolymer and mixtures thereof, with at least one co-film forming agent chosen from an epoxy resin, imparts good adhesion, long wear and high gloss to nail polish compositions, in the absence of nitrocellulose.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, an item of clothing. Transfer resistance may be evaluated by any method known in the art for evaluating such. For example, transfer resistance of a composition may be evaluated by a modified "kiss" test. The modified "kiss" test may involve application of the composition to a fingernail followed by rubbing a material, for example, a sheet of paper, against the nail after expiration of a certain amount of time following application, such as 5 minutes after application. Similarly, transfer resistance of a composition may be evaluated by the amount of product transferred from a wearer to any other substrate, such as transfer from the nail of an individual to a sleeve when putting on clothing after the expiration of a certain amount of time following application of the composition to the nail. The amount of composition transferred to the substrate (e.g., sleeve or paper) may then be evaluated and compared. For example, a composition may be transfer resistant if a majority of the product is left on the wearer's nails. Further, the amount transferred may be compared with that transferred by other compositions, such as commercially available compositions. In a preferred embodiment of the present invention, little or no composition is transferred to the substrate from the nail.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

The compositions and methods of the present invention can comprise, consist of, or consist essentially of the essential elements and limitations of the invention described herein, as well as any additional or optional ingredients, components, or limitations described herein or otherwise useful.

High Gloss Film Forming Agent

According to the present invention, compositions comprising at least one high gloss film forming agent are provided. In particular, according to the present invention, the at least one high gloss film forming agent comprises optionally-esterified styrene maleic anhydride copolymers. "Styrene maleic anhydride copolymer," as used herein, means any polymer obtained by copolymerization of one or more maleic anhydride comonomers and of one or more styrene comonomers, the maleic anhydride comonomers optionally being partially or completely hydrolysed.

In general, it is known that while optionally-esterified styrene maleic anhydride copolymers have good adhesion and high gloss, they have a tendency to be too brittle. Their use, therefore, has typically been limited to those applications where brittleness is not a concern. The inventors, however, have surprisingly found that optionally-esterified styrene maleic anhydride copolymers, when mixed with certain softer co-film forming agents, may then be effectively employed in nail polish compositions in spite of their conventional brittle tendencies. It has been found that such combinations allow for a nail composition to be formulated, in the absence of nitrocellulose, having long wear, good adhesion and high gloss properties, above and beyond conventional nail polish compositions containing nitrocellulose.

According to preferred embodiments, the optionally-esterified styrene maleic anhydride copolymer has a molar fraction of maleic anhydride units of between 0.1 and 0.95, more preferably between 0.4 and 0.9.

According to preferred embodiments, the optionally-esterified styrene maleic anhydride copolymer has styrene and maleic anhydride monomers in a molar ratio of 1:3 to 3:1, more preferably in a molar ratio of 1:2 to 2:1, and more preferably in a molar ratio of about 1:1, including all ranges and subranges therebetween such as 1.2:1 and 1.4:1.

According to preferred embodiments, the optionally-esterified styrene maleic anhydride copolymer has a weight-average molecular weight ranging from about 5,000 to 500,000, preferably from about 10,000 to 300,000, and most preferably from about 100,000 to 200,000.

According to preferred embodiments, the optionally-esterified styrene maleic anhydride copolymer has a glass transition temperature (Tg) ranging from about 100° C. to 175° C., preferably from about 125° C. to 160° C., and more preferably from about 135° C. to 155° C.

"Esterified styrene maleic anhydride copolymer" as used herein means a styrene maleic anhydride copolymer which has been esterified using a small alcohol compound. Preferably, the small alcohol compound has fewer than 8 carbon atoms, preferably fewer than five carbon atoms, and more preferably fewer than four carbon atoms. For example, a styrene maleic anhydride copolymer can be esterified via standard esterification techniques using butanol, isobutanol, propanol, isopropanol, ethanol, methanol or any mixture of these alcohols, to produce an esterified styrene maleic anhydride copolymer. Such esterification does not have to be complete. Rather, partial esterification can occur and, in fact, is preferred in accordance with the present invention.

Particularly preferred esterified styrene maleic anhydride copolymers include, but are not limited to, those available from Hercules under the Scripset® name. Such commercially available products include solid powder products such as, for example, Scripset® 540, Scripset® 550 and Scripset® 810, as well as liquid solutions containing the polymers such as, for example, imPress® SC-745 (sodium solution) and imPress® SC-740 (ammonium solution). An example of a particularly preferred esterified styrene maleic anhydride copolymer is a mixed methyl and isobutyl partial ester sold under the name Scripset® 540.

Suitable examples of non-esterified styrene maleic anhydride copolymers include, but are not limited to, Hercules products Scripset® 520 (styrene/maleic anhydride copolymer), as well as liquid solutions containing this polymer such as, for example, imPress® SC-700 (sodium solution) and imPress® SC-720 (ammonium solution); Atofina products such as the styrene/maleic anhydride (50/50) copolymer, in the form of an ammonium salt at 30% in water, sold under the reference SMA1000H® or the styrene/maleic anhydride (50/50) copolymer, in the form of a sodium salt at 40% in water, sold under the reference SMA1000HNa®; and Sartomer products such as SMA® 1000 (styrene/maleic anhydride (50/50) copolymer having a Tg of 155° C., a Mn of 2000, and a Mw of 5500), SMA®2000 (styrene/maleic anhydride (2:1) copolymer having a Tg of 135° C., a Mn of 3000, and a Mw of 7500), and SMA®2021 (styrene/maleic anhydride (2:1) copolymer having a Tg of 155° C., a Mn of 12,000, and a Mw of 21,000).

In accordance with preferred embodiments, the at least one high gloss film-forming agent of the present invention is preferably present in the composition in an amount of from about 1% to about 40% by weight, preferably from about 5% to about 30% by weight, and more preferably from about 10% to about 20% of the total weight of the composition, including all ranges and subranges therebetween, all weights based on the total weight of the composition.

Co-Film Forming Agents

According to particularly preferred embodiments of the present application, compositions further comprising at least one co-film forming agent chosen from an epoxy resin are provided. Particularly preferred epoxy resins include, but are not limited to, tosylamide epoxy resins such as those sold under the Polytex name by Estron Chemical, Inc. (for example, E-75, E-100 and NX-55). Epoxy resins have been shown to provide good adhesion and are less brittle than the high gloss film forming agents disclosed above.

Other co-film forming agents that may be employed in combination with an epoxy resin include, for example, radical polymers, polycondensates and polymers of natural origin.

Examples of suitable co-film forming agents include, but are not limited to, vinyl polymers such as, for example, polyvinyl butyral, acrylic (co)polymers, acrylic resins, styrene resins, acrylate-styrene resins, vinyl resins, vinyl copolymers, polyurethanes, polyesters, alkyd resins, cellulose polymers, such as nitrocellulose, cellulose esters, such as cellulose acetate, cellulose acetate propionate or cellulose acetate butyrate, resins resulting from the condensation of formaldehyde with an arylsulphonamide, and their mixtures. Other suitable co-film forming polymers may also include film formers which are more compatible with water. Examples of such film formers include, but are not limited to, starches and derivatives thereof, natural or synthetic gums and derivatives thereof, water soluble adhesives. Particularly preferred co-film forming agents are resin film forming agents, particularly polyester, acrylic and acrylic resins.

Specific examples of useful (meth)acrylic polymers or resins include, but are not limited to, copolymers of methyl methacrylate with butyl acrylate, butyl methacrylate, isobutyl methacrylate, or isobornyl methacrylate (e.g., PARALOID DM-55, PARALOID B48N, PARALOID B66, ELVACITE 2550), copolymers of isobutylmethacrylate and butyl methacrylate (e.g., ELVACITE 2046), and isobutyl methacrylate polymers (e.g., PARALOID B67).

Specific examples of polyester resins include, but are not limited to, polyester resins formed by reacting a polyhydric alcohol with a polybasic acid, e.g., phthalic acid such as, for example, UNIPLEX 670-P polyester resin, which is available from Unitex Chemical Corporation and which is a polyester resin obtained by reacting trimellitic acid, neopentyl glycol, and adipic acid.

As stated above, optionally-esterified styrene maleic anhydride copolymers are known to be brittle. However, it has been surprisingly found that combining them with at least one co-film forming agent chosen from an epoxy resin effectively renders the optionally-esterified styrene maleic anhydride copolymer less brittle, thereby allowing it to be incorporated into nail polish compositions having long wear, good adhesion and high gloss properties, without requiring the use of nitrocellulose. Accordingly, it is preferred that the at least one co-film forming agent chosen from an epoxy resin has a glass transition temperature (Tg) of less than about 100° C., preferably less than about 80° C.

According to preferred embodiments, the at least one co-film forming agent chosen from an epoxy resin is present in the compositions of the present invention in an amount ranging from about 0.1 to about 50% by weight, more preferably from about 1 to about 40% by weight, and most preferably from about 10 to about 30% by weight, including all ranges and subranges therebetween, all weights based on the total weight of the composition.

According to preferred embodiments, the compositions of the present invention contain weight ratios of optionally-esterified styrene maleic anhydride copolymer to at least one co-film forming agent chosen from an epoxy resin ranging from about 1 to 1, preferably from about 2 to 1, and more preferably from about 3 to about 1, including all ranges and subranges therebetween.

According to yet other preferred embodiments, the compositions of the present invention contain weight ratios of optionally-esterified styrene maleic anhydride copolymer to at least one co-film forming agent chosen from an epoxy resin in a range of about 1 to 1, preferably about 1 to 2, and more preferably about 1 to 3, including all ranges and subranges therebetween.

Plasticizer

According to particularly preferred embodiments of the present invention, compositions further comprising at least one plasticizer are provided. Any plasticizing agent typically found in nail polish compositions can be used. Examples of suitable plasticizers include, but are not limited to, glycols and their ether or ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

In accordance with preferred embodiments, the plasticizer, is preferably present in the composition in an amount of from about 0.01% to about 25% by weight, preferably from about 0.1% to about 22% by weight, preferably from about 1 to about 20% by weight, including all ranges and subranges therebetween, all weights based on the total weight of the composition.

Solvent

Any solvent typically found in nail polish compositions can be used. Suitable solvents include, but are not limited to, organic solvents which are liquid at ambient temperature. Examples of suitable solvents include, but are not limited to, ketones such as methyl ethyl ketone, methyl isobutyl ketone, diisobutyl ketone, isophorone, cyclohexanone or acetone; alcohols, such as ethanol, isopropanol, diacetone alcohol, 2-butoxyethanol or cyclohexanol; glycols, such as ethylene glycol, propylene glycol, pentylene glycol or glycerol; propylene glycol ethers, such as propylene glycol monomethyl ether, propylene glycol monomethyl ether acetate or dipropylene glycol mono(n-butyl)ether; short-chain esters (having a total of 2 to 7 carbon atoms), such as ethyl acetate, methyl acetate, propyl acetate, n-butyl acetate or isopentyl acetate; alkanes, such as decane, heptane, dodecane or cyclohexane; aldehydes, such as benzaldehyde or acetaldehyde; water and their mixtures. Most preferred are short-chain esters (having a total of from 2 to 8 carbon atoms).

In accordance with preferred embodiments, the solvent, is preferably present in the composition in an amount of from about 1% to about 90% by weight, preferably from about 10% to about 80% by weight, preferably from about 30 to about 75% by weight, including all ranges and subranges therebetween, all weights based on the total weight of the composition.

Colorant

According to particularly preferred embodiments of the present application, compositions further comprising at least one colorant are provided. Any colorant typically found in nail polish compositions can be used. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments, the colorant, if present, is preferably present in the composition in an amount of from about 0.01% to about 20% by weight, preferably from about 0.1% to about 15% by weight, preferably from about 0.5 to about 10% by weight, including all ranges and subranges therebetween, all weights based on the total weight of the composition.

Auxiliaries/Additives

The nail polish composition of the present invention may additionally comprise an additive or auxiliary commonly used in cosmetic compositions and known to a person skilled in the art as being capable of being incorporated into a nail polish composition. Such additives or auxiliaries may be chosen from thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amounts thereof such that the advantageous properties of the composition according to the invention are not, or are not substantially, adversely affected by the envisaged addition.

These substances may be selected variously by the person skilled in the art in order to prepare a composition which has the desired properties, for example, good adhesion or long wear.

These additives may be present in the composition in an amount of up to about 99% by weight (such as from about 0.01% to about 90%) relative to the total weight of the composition, and further such as from about 0.1% to about 50% (if present), including all ranges and subranges therebetween.

Needless to say, the composition of the invention should be cosmetically or dermatologically acceptable, i.e., it should contain non-toxic physiologically acceptable components. The composition may be in any galenic form normally employed in the cosmetic and dermatological fields which is suitable for topical administration onto nails.

One particularly preferred embodiment of the present invention is a composition for application to nails which is substantially free of nitrocellulose (that is, less than 5% of nitrocellulose), essentially free of nitrocellulose (that is, less than 2% nitrocellulose), or free of nitrocellulose (that is, less than 0.25% nitrocellulose).

It has been surprisingly found that the inventive compositions provide a degree of gloss that is at least comparable, and oftentimes higher, than that of conventional nitrocellulose-containing compositions. Accordingly, the compositions of the present invention have gloss values of at least 80 at angles of 60° and 20°.

According to preferred embodiments of the present invention, methods of making up or protecting nails comprising applying a composition of the present invention to nails in an amount sufficient to makeup or protect the nails are provided. "Making up" as used herein means to provide decoration (for example, color) to the nail. "Protecting" as used herein means to inhibit damage to the nail (for example, chipping) by providing a protective layer on the nail.

In accordance with a preferred embodiment of the preceding methods, a composition of the present invention comprising at least one high gloss film forming agent chosen from an esterified styrene maleic anhydride copolymer, a non-esterified styrene maleic anhydride copolymer, and mixtures thereof; at least one co-film forming agent chosen from an epoxy resin; at least one solvent; optionally, at least one plasticizer; and, optionally, at least one colorant, is applied topically onto the nails of a person in order to makeup and/or protect said nails, in an amount sufficient to achieve the desired result. The compositions may be applied to the desired area as needed, preferably once every 3 to 5 days.

The compositions according to the invention can be manufactured by known processes used generally in the cosmetics or dermatological field. For example, a first composition comprising at least one optionally-esterified styrene maleic anhydride copolymer and at least one solvent can be prepared, and a second composition comprising at least one co-film forming agent and at least one plasticizer can be prepared. Then, the two compositions can be combined, optionally with additional solvent. Of course, the relative amounts of first and second compositions combined would likely depend on the amounts of ingredients desired in the final combined composition.

The following examples are intended to illustrate the invention without limiting the scope as a result. The percentages are given on a weight basis.

EXAMPLES

Examples 1-3

| Phase | Chemical Name | Trade Name | EX 1 % | EX 2 % | EX 3 % |
|---|---|---|---|---|---|
| A | Styrene Maleic Copolymers | Scripset 550 | 30 | | 30 |
| A | Styrene Maleic Copolymers | Scripset 540 | | 30 | |
| A | Ethyl Acetate | | 35 | 35 | 35 |
| A | Propyl Acetate | | 35 | 35 | 35 |
| | | TOTAL | 100 | 100 | 100 |
| B | Scripset 550 solution from Phase A | | 50 | | 53.5 |
| B | Scripset 540 solution from Phase A | | | 50 | |
| B | Tosylamide Epoxy Resin (75% solid/butyl acetate) | Polytex NX-55 | 20 | 20 | 21.4 |
| B | Butyl Acetate | | 30 | 30 | 13.4 |
| B | Red 7 color pigment | | | | 11.7 |
| | | total % | 100 | 100 | 100 |
| | Gloss value at angle of 20° | | 91.2 | 91.2 | 84.4 |
| | Gloss value at angle of 60° | | 96.3 | 95.9 | 94.8 |

1. The ingredients of phase A were combined and mixed at room temperature at a sheer rate of 200-300 rpm for 1 hr until a homogenous solution was seen.

2. Phase B was added to phase A with stirring for 5-10 minutes to form the resultant nail polish composition.

Example 4-7

| Phase | Chemical Name | Tradename | EX 4 % | EX 5 % | EX 6 % | EX 7 % |
|---|---|---|---|---|---|---|
| A | Styrene maleic anhydride copolymer | SMA 2021P | 45 | 45 | 45 | 45 |
| A | Ethyl Acetate | | 27.5 | 27.5 | 27.5 | 27.5 |
| A | Propyl Acetate | | 27.5 | 27.5 | 27.5 | 27.5 |
| | total %: | | 100 | 100 | 100 | 100 |
| B | SMA 2021P Prep | SMA 2021P | 48 | 47.5 | 41.5 | 31.3 |
| B | Butyl Acetate | | 29 | | | |
| B | Ethyl Acetate | | | 10.9 | 15.15 | 21 |
| B | Propyl Acetate | | | 10.9 | 15.15 | 21 |
| B | Tosylamide Epoxy Resin | NX55 Polytex | 23 | 19 | 16.5 | 15 |
| B | Cellulose Acetate Butyrate Color chip | | | 11.7 | 11.7 | 11.7 |
| | total % | | 100 | 100 | 100 | 100 |
| | Gloss value at angle of 20° | | 95.7 | 86.3 | 89.1 | 87.3 |
| | Gloss value at angle of 60° | | 98.7 | 96.6 | 96.6 | 96.9 |

1. Ingredients of phase A were combined and mixed at a sheer rate of 200-300 rpm for 1 hr until a homogenous solution was seen.
2. Phase B was added and mixed in a paint shaker for 5-10 minutes until uniformity was observed.

Comparative Formulations (CF) 1-2:
Nitrocellulose-Containing Formulations

| Chemical Name | CF 1 % | CF 2 % |
|---|---|---|
| Nitrocellulose ½ Sec (40% Solids in 60% Ethyl Acetate) | 26.58 | 26.58 |
| Nitrocellulose ⅝ sec (20% Solids in 80% Butyl Acetate) | 21.15 | 21.15 |
| Isopropyl Alcohol | 0.187 | 0.187 |
| Propyl Acetate | 4.00 | 3.5 |
| Butyl Acetate | 3.47 | 3.47 |
| Ethyl Acetate | 30.08 | 15.08 |
| Tosylamide Epoxy Resin | 2.607 | 2.607 |
| Ethyl Tosylamide | 2.615 | 2.615 |
| Acrylates Copolymer | 1.758 | 1.758 |
| ADIPIC ACID/NEOPENTYL GLYCOL/TRIMELLITIC ANHYDRIDE COPOLYMER | 2.607 | 2.607 |
| Triphenyl Phosphate | 4.95 | 4.95 |
| Red 7 color monochrome | | 15.5 |
| Total | 100.00 | 100.00 |
| Gloss value at angle of 20° | 82 | 76.6 |
| Gloss value at angle of 60° | 94 | 88.6 |

1. The Nitrocellulose (½ Sec and ⅝ Second) was added along with Isopropyl Alcohol, Propyl Acetate, Butyl Acetate, Ethyl Acetate.
2. Ethyl Tosylamide Epoxy Resin, Ethyl Tosylamide, Acrylates Copolymer, Adipoc Anhydride Copolymer and Triphenyl Phosphate were added and mixed in a paint shaker for 5-10 minutes. For comparative formulation 2, the pigment was also added.

Gloss Measurements:
Readings for Clear Compositions

| | EX 1 | EX 2 | EX 4 | CF 1 |
|---|---|---|---|---|
| Gloss value at angle of 20° | 91.2 | 91.2 | 95.7 | 82 |
| Gloss value at angle of 60° | 96.3 | 95.9 | 98.7 | 94 |

Readings for Color Compositions

| | EX 3 | EX 5 | EX 6 | EX 7 | CF 2 |
|---|---|---|---|---|---|
| Gloss value at angle of 20° | 84.4 | 86.3 | 89.1 | 87.3 | 76.6 |
| Gloss value at angle of 60° | 94.8 | 96.6 | 96.6 | 96.9 | 88.6 |

Procedure for Measuring Gloss:
1. A Leneta Card was placed on a flat vacuum plate, and then nail polish was poured thereon.
2. A 3 mil Bird applicator was used to draw down the solutions of the samples on a Leneta Contrast Card Form 5C—H.
3. The drawdown sample was left to dry for 2 hrs.
4. Gloss Measurements (at 20°, 60°) were taken using a BYK Gardner Micro-Tri-Gloss meter.
5. The gloss measurements were taken over the black substrate of the Leneta Card. The mean value was recorded on 3 different parts of the film.

With respect to clear nail composition examples 1, 2 and 4, gloss values were all over 90 at angles of 60° and 20°. However, the comparative nitrocellulose containing formula CF 1 had a gloss value of only about 82 at an angle of 20°. Thus, the inventive compositions have higher overall gloss values.

Regarding color nail composition examples 3, 5, 6 and 7, the gloss values at 20° were all over 80. The comparative nitrocellulose containing formula CF2, on the other hand, had a gloss value of only about 76. Further, gloss values for color nail composition examples 3, 5, 6 and 7, at 60°, were all over 90. In contrast, the comparative nitrocellulose containing formula CF2 had a gloss value of about 88. Thus, here too, with respect to colored nail compositions, it can be seen that the inventive compositions have higher overall gloss values as compared to conventional nitrocellulose-containing compositions.

What is claimed is:
1. A nail polish composition, comprising:
   a. at least one high gloss film forming agent chosen from (1) an esterified styrene maleic anhydride copolymer selected from mixed methyl and isobutyl partial ester copolymers, (2) a non-esterified styrene maleic anhydride copolymer, and mixtures thereof, each of said copolymers having a styrene/maleic anhydride monomer molar ratio of from 1:2 to 2:1, and mixtures thereof, said film forming agent being present in an amount from about 10% to about 20% by weight of the total composition, having a molecular weight from about 5,000 to about 200,000 and having a Tg ranging from about 125° C. to about 160° C.;
   b. a tosylamide epoxy resin having a Tg of less than about 80° C. and being present in an amount ranging from about 11% to about 20% of the total weight of the composition;

c. at least one plasticizer being present in an amount of from about 1% to about 20% by weight, based on the total weight of the composition;
d. at least one solvent, said solvent being present in an amount of from about 10% to about 80% by weight, based on the total weight of the composition; and
e. optionally, at least one colorant;
wherein the weight ratio of the high gloss film forming agent to the at least one co-film forming agent is from about 1 to 1 to about 2 to 1, said composition having a gloss value of at least 80 at angles of 20° and 60° and containing about 0% nitrocellulose.

2. The composition of claim 1, wherein the at least one high gloss film forming agent is a mixed methyl and isobutyl partial ester.

3. The composition of claim 1, wherein the at least one solvent is chosen from ethyl acetate, propyl acetate, butyl acetate, and mixtures thereof.

4. A method of making up or protecting nails comprising applying onto the nails the nail polish composition of claim 1.

5. The method of claim 4, wherein the at least one high gloss film forming agent is a mixed methyl and isobutyl partial ester.

6. The method of claim 4, wherein the at least one solvent is chosen from ethyl acetate, propyl acetate, butyl acetate and mixtures thereof.

* * * * *